United States Patent [19]

Charatan

[11] Patent Number: 4,519,408
[45] Date of Patent: May 28, 1985

[54] ORAL HYGIENE DEVICE

[76] Inventor: Norman Charatan, 22 Varady Dr., Fords, N.J. 08863

[21] Appl. No.: 507,220

[22] Filed: Jun. 24, 1983

[51] Int. Cl.³ ............................................. A61C 15/00
[52] U.S. Cl. .......................................... 132/89; 132/93
[58] Field of Search .................. 132/89, 90, 91, 92 R, 132/92 A, 93; 401/134

[56] References Cited

U.S. PATENT DOCUMENTS

| | | | |
|---|---|---|---|
| 3,696,821 | 10/1972 | Adams | 132/91 |
| 3,860,013 | 1/1975 | Czapor | 132/91 |
| 3,896,808 | 7/1975 | Szpur | 401/134 |
| 3,901,251 | 8/1975 | Johnston | 132/91 |
| 4,403,625 | 9/1983 | Sanders et al. | 132/91 |

Primary Examiner—Richard J. Apley
Assistant Examiner—Carolyn A. Harrison
Attorney, Agent, or Firm—Robert D. Farkas

[57] ABSTRACT

An oral hygiene device is comprised of a hollow housing, having a weakened section in the periphery of the housing so that when the weakened section is broken, a user may grasp and separate the housing into two portions. A length of dental floss-like material is totally encased within a cavity in the unbroken housing and is secured at each end to two interior regions of the housing that are separated by the weakened section. The length of the dental floss-like element is sufficient to allow the two portions of the housing to be grasped with opposite hands of the user and disposed in spaced apart relationship with each other, thereby permitting the precoiled portion of the floss-like material to be straightened out and to be applied between adjacent teeth of the user, in conventional fashion.

8 Claims, 12 Drawing Figures

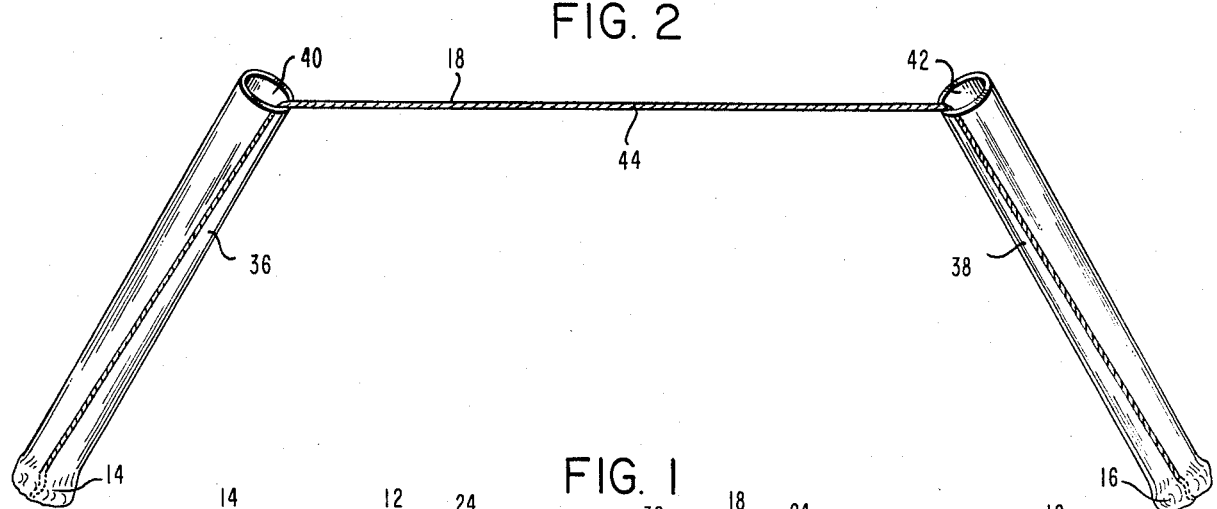
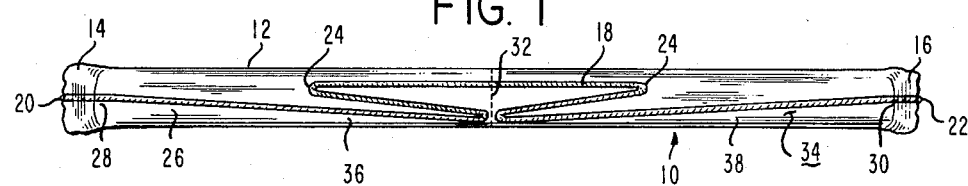
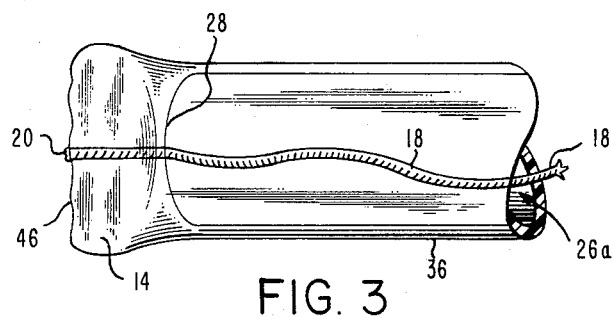
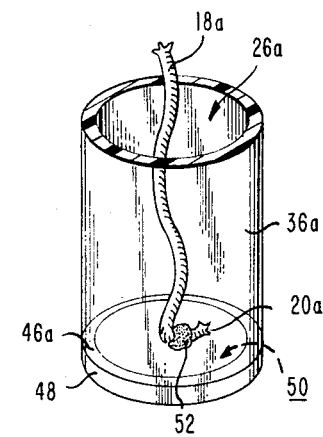
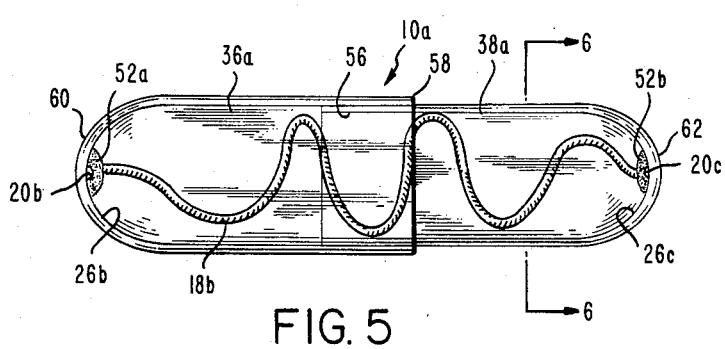
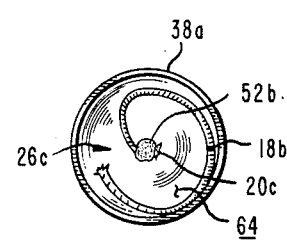

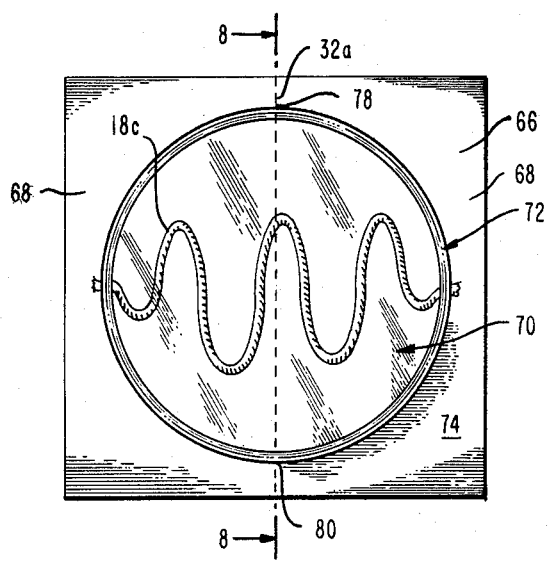
FIG. 7
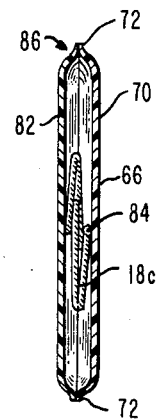
FIG. 8
FIG. 10
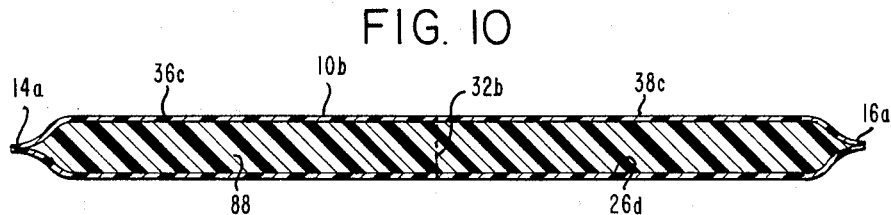
FIG. 9
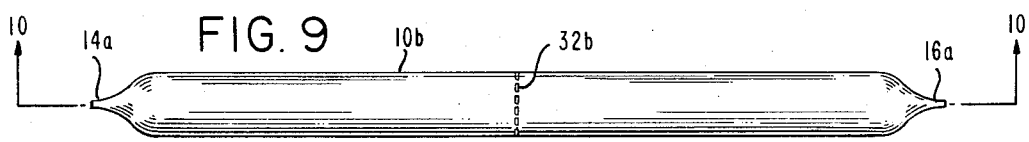
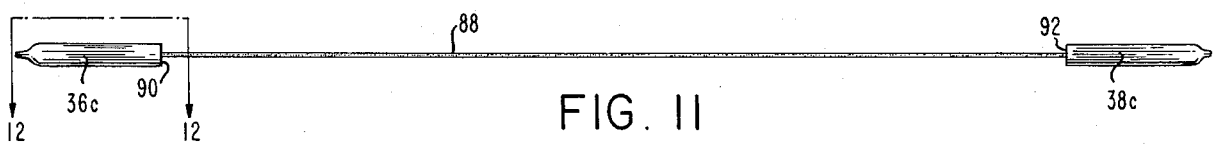
FIG. 11
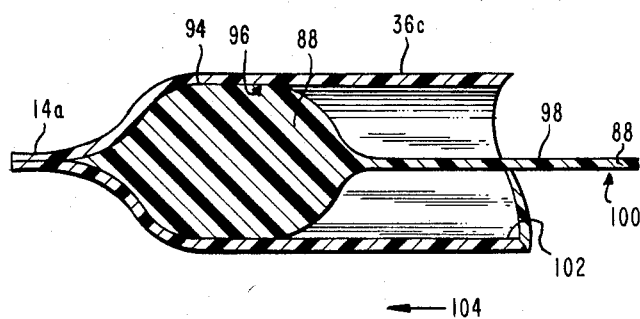
FIG. 12

ORAL HYGIENE DEVICE

BACKGROUND OF THE INVENTION

1. The Field of the Invention

This invention concerns dental floss devices and the manner in which they may be used for preventative and corrective dental care. This invention further concerns dental floss containers, of the one-time use variety, serving also as handles by which the user may manipulate and use the device.

2. Description of the Prior Art

The prior art abounds with devices which concern the use of dental floss. U.S. Pat. No. 2,982,264, issued Apr. 25, 1961, by A. F. De Felice, teaches a dental cleaner massager, wherein such massager utilizes a floss member of conventional construction, secured to the apex of two cone-like shaped bodies fabricated from an elastomeric material. In use, the length of the dental floss, extending between the apex of the cones, pass between the teeth of the user so as to permit the tapered sharp cone to enter into the space between the teeth, further enhancing the cleaning process and providing for massaging. The cones act as handles for the apparatus. In use, the De Felice device requires a container to house a portion of the dental floss to be applied to the teeth, and presumptively, at least portions of one of the cones that may come in contact with the mouth of the user for sanitary purposes.

U.S. Pat. No. 2,443,415, issued June 15, 1948 to J. Buscarino describes a dental floss holder, which holder has a finger grasping portion and an anvil affixed thereto. Secured to the distal most ends of the open ended anvil is a section of dental floss. Unfortunately, such apparatus utilizes a segment of dental floss which is pre-stretched and defined as to length, for all applications. Further, the Buscarino teaching fails to describe means to maintain the anvil portion, which is insertable into the mouth of the user, in a clean condition, either between uses or prior to its first use.

U.S. Pat. No. 3,696,821 issued Oct. 10, 1972 to John Q. Adams, IV, discloses a pair of caps or thimbles that engage over two fingers of the user, the closed ends of the thimbles being apertured to allow feeding of the dental floss therethrough, from the supply container—as is required to clean teeth. The thimbles functionally clamp the dental floss to the fingers so that the floss may be properly tensioned for use without the inconvenience and frequent discomfort which arises when the dental floss is wound around the fingertips. In one embodiment, Adams describes the thimble carrying the dental floss being stored within the two thimbles, when such thimbles are disposed having their open mouth portions adjacent one another. Since the thimbles themselves must be threaded, in their use, and the thimbles may come into contact with the interior portions of the mouth of the user, the thimbles and the handled portions of the dental floss, being dispensed from the spool, must be kept clean in order to insure the safety and convenience of the user. The Adams teaching fails to provide for this problem.

U.S. Pat. No. 4,016,892 issued Apr. 12, 1977 to Ingram S. Chodorow, describes a dental flossing device utilizing a segment or strand of dental floss with two gripping means secured to the segment and spaced apart a fixed distance. The grippers are dimensioned to be suitable for grasping between two fingers of the user's hand. Chodorow describes techniques for fastening the grippers to long lengths of the floss material such that a spool consisting of many grippers and an extended length of dental floss may be stored within the container. The container is provided with an opening through which selected lengths of the floss-gripper combinations may be dispensed and separated from the bulk of the composite assembly, stored on the spool, prior to use.

In all of the above described disclosures, no teaching illustrates an apparatus in which a cut length of dental floss is secured at the two free ends of the dental floss, to a housing containing same. No housing is taught which, when broken apart, serves as handles for manual grasping use, nor serves as a storage mechanism for a finite length of dental floss which has an unextended length greater than the distance separating the portions of the intact housing to which each end of the dental floss is secured.

SUMMARY OF THE INVENTION

The present invention overcomes the problems posed by the prior art and succeeds in accomplishing the objects hereinabove set forth by providing a housing, having a closed configuration. Such housing contains therewithin a length of material, of conventional dental-floss variety, or, of any material in elongated form, preferably bondable or flexible, which is suitable for flossing purposes. The floss material has its two ends secured to the housing at two diverse locations. Intermediate such two locations may be a weakened portion of the housing. The weakened portion of the housing extends about the periphery of the housing such that two contiguous housing portions, comprising the housing, when the housing is separated at the weakened portion, provides such two housing portions that are each graspable by opposite hands of the user. The floss material extends between, and is connected to, the two housing portions. Such exposed floss material, prior to the separation of the housing into its two portions, was totally encapsulated within the intact housing. The two portions of the housing may serve as handles. There are no free ends of floss-like material to deal with, nor is there any need to thread any portion of the dental floss-like material into any apertures of the portions serving as handles. After use, because of the economical construction above described, the user may discard the entire apparatus. Extensible floss materials may be utilized. Any shaped housings may also be selected, dependent upon the application. In one embodiment of the present invention, the housing utilizes two separable housing elements which are joined together in telescope fashion. The ends of the floss-like material are secured within each telescoping element, each of which, when joined together forms a single cavity for totally housing the floss-like material. In another embodiment of the present invention, an extensible elastomeric material fills the cavity comprising the intact housing such that when the housing is broken at its weakened area, the elastomeric material may be extended so as to provide a dental floss-like material whose cross sectional shape may be selected to suit any particular gum or tooth cleaning application.

These objects as well as other objects of the present invention, will become still more readily apparent after reading the following description of the accompanying drawings.

BRIEF DESCRIPTION OF THE DRAWINGS

FIG. 1 is a side elevation view of an embodiment of the present invention.

FIG. 2 is a perspective view of the apparatus shown in FIG. 1, after the housing portion has been separated.

FIG. 3 is a side elevation view of a portion of the apparatus shown in FIG. 2.

FIG. 4 is a perspective view of a portion of an alternate embodiment of the apparatus that is shown in FIG. 1.

FIG. 5 is a side elevation view of yet another embodiment of the apparatus that is shown in FIG. 1.

FIG. 6 is a side elevation cross-sectional view, taken along lines 6—6, viewed in the direction of arrows 6—6, of the apparatus shown in FIG. 5.

FIG. 7 is still another embodiment of the present invention, shown in side elevation view, from the embodiment shown in FIG. 1.

FIG. 8 is a side elevation cross-sectional view, taken along lines 8—8, viewed in the direction of arrows 8—8, of the apparatus shown in FIG. 7.

FIG. 9 is yet another embodiment of the present invention, shown in side elevation view.

FIG. 10 is a side elevation cross-sectional view, taken along lines 10—10, viewed in the direction of arrows 10—10, of the apparatus shown in FIG. 9.

FIG. 11 is a side elevation view of the apparatus shown in FIG. 9 when such apparatus has the housing portions thereof separated and pulled apart.

FIG. 12 is a side elevation cross-sectional view, of a portion of the apparatus shown in FIG. 11, viewed along lines 12—12 in the direction of arrows 12—12.

DESCRIPTION OF THE PREFERRED EMBODIMENT

The structure and method of fabrication of the present invention is applicable to a housing, preferably fabricated from a right angle cylinder. The housing may be constructed from a plastic material, such as polyethylene or polypropylene. The housing may be transparent or opaque—as desired. The housing should have a length of approximately an inch and a half to three and a half inches, with a diameter of approximately three-sixteenths of an inch, O.D. Disposed within a cavity ormed by such housing is a length of dental floss-like material, being fabricated from a wide variety of materials. Such materials may include multi-filament nylon, cotton thread, mono-filament thread, fishing line, metal wire, stretched rubber bands, waxed string, and any other material, being natural or plastic, which has a circular or flattened cross-section, suitable for introduction between the teeth of a user. The housing has a weakened portion, preferably made by a series of continuous, spaced apart non-piercing serrations, extending around the periphery of the housing in an annular shape defining a plane transverse to the longitudinal axis of the housing. Each end of the floss-like material is secured at or close to the closed ends of the housing such as by utilizing heat sealing, adhesive, or the like. The ends of the housing, may be pinched together about the ends of the floss-like material, so as to entirely capture the three portion of the floss-like material within the confines of the cavity formed by the housing, before the housing is broken.

In another embodiment of the present invention, a cylindrical housing has its open ends closed by adhering thereto circular discs, to which the ends of the floss-like material are secured.

In another embodiment of the present invention, the housing is fabricated from two right angle cylinders, each of which has one end closed, as by casting, molding, heat sealing or the like. The open end of one of such right angle cylinders is insertable, in telescoping fashion, within the open end of the other cylinder. A unitary portion or length of dental floss is confined within a cavity formed by each of the cavities of each cylindrical element, and has the free ends thereof secured at adjacent opposite ends of the two cylindrical portions. In use, the user grasps each of the two separable portions of the housing, applies a force in opposite directions thereto, and exposes—for the first time—a useable portion of the length of the dental floss thereinbetween, leaving the two cylindrical portions available for use as handles.

A suitable housing may be fabricated from two flattened sheets of plastic material, such that the sheets are secured together—as by heat sealing or by adhesive means—thereby forming a single structure having a cavity in the interior portions and waste material extending outwardly therefrom. By severing the waste material and discarding same, a housing is provided which has a substantially flat shape. The floss-like material may be secured within the cavity, at opposite sides of the shape, during the sealing or adhesive process. A weakened portion of the housing, extending along the entirety of both lateral faces, permits the user to separate the flattened housing into two portions, exposing the therebefore totally protected extensible length of dental floss for immediate use.

Another embodiment of the present invention utilizes a housing, having any desired shape, though preferably fabricated from a hollow right angle cylinder whose opposite ends are sealed closed. Placed within such housing is an elastomeric material, such as ethylene propylene copolymer, such as VISTALON 404, manufactured by Exxon Chemical Company of Houston, Tex., U.S.A.; or ethylene-vinyl acetate copolymers, such as ELVAX, a product of the Dupont Company, Wilmington, Del., U.S.A.; or low density polyethylene elastomer compounds, equivalent to Heisler Compound HC5201, a product of Heisler Compounding Division Container Corporation of America, Wilmington, Del., U.S.A. Such materials are noted to have the capability of being manually extendable when a force is applied along its length. At some point, such materials reach a given maximum length, having then a foreshortened diameter. The ability to continually stretch such materials is limited, such that the material achieves a much greater tensile strength at the time of its maximum elongation. I have fabricated test samples of these materials and note that the such materials tend to remain adhered to the interior of plastic housings, in the regions adjacent the closed end of the cylindrical housing, yet tend to stretch in the central region adjacent to the weakened and broken portion of the housing. No adhesive is absolutely required to secure these stretchable elastomeric materials to the interior of a rigid housing since the stretched portions thereof reach a maximum tensile strength point, prior to the time that the remaining unextended elastomeric material, attached to each housing portion, is separated from each housing portion. Further experiments indicate that cavities of housings that have rectangular cross-sections, tend to yield a stretched material, disposed between the two fractured portions of the housing, that is similarly rectangular in shape but whose dimensions are substantially smaller than the rectangular interior cross-section of the housing. In any event, the elastomeric stretchable embodiment of the present invention has its ends secured to each portion of the housing before and during the use of the apparatus.

Now referring to the figures, and more particularly to the embodiment illustrated in FIG. 1 showing the present invention 10 fabricating a rigid housing 12 from a transparent material. The housing, if desired, can be fabricated from a flexible plastic material, such as polyethylene film. End 14 and end 16 of housing 12 are shown in a flattened shape. Dental floss-like material 18 is shown disposed within the interior of housing 12 having ends 20 and 22 secured within flattened portions 14 and 16 respectively. Loops 24 of dental floss-like material 18 permit a length of dental floss 18 to be contained within cavity portions 26 of housing 12, having a greater length than the distance separating points 28 and 30 of housing 12. Dotted lines 32 are disposed in surface 34 of housing 12, intermediate points 28 and 30. Portion 36 and 38 are disposed on opposite sides of weakened portion 32 and together define the entirety of housing 12.

FIG. 2 illustrates portions 36 and 38 of housing 12—shown in FIG. 1, in separated condition. Open mouth regions 40 and 42 of portions 36 and 38, permit dental floss 18 to emerge therefrom such that portion 44 of dental floss 18 may be disposed along a straight line.

FIG. 3 illustrates cavity portion 26a of cavity 26 shown in FIG. 1. It can be seen that end 20 of floss 18 ends substantially at end 46 of housing portion 36.

FIG. 4 illustrates an embodiment of the present invention utilizing housing portion 36a, similar to housing portion 36 shown in FIG. 1, but having annular disc 48 secured to end 46a of housing portion 36a, as by heat sealing, adhesives, or spin welding techniques. End point 20a, of dental floss material 18a, is shown secured to surface 50, of disc 48, by any convenient means, and more particularly by adhesive 52. In all other respects, the apparatus indicated in FIG. 4 may be similarly constructed to that shown in FIG. 1, excepting that end 22 of dental floss 18 would be secured to an equivalent disc 48.

FIG. 5 illustrates a housing 10a, comprising parts 36a and 38a. Part 38a has region 56 thereof insertable within region 58 of housing part 36a, as by sliding—in a telescopic fashion. Dental floss element 18b is shown secured within cavities 26b and 26c, of housing portions 36a and 38a respectively, as by having ends 20b and 20c secured to closed ends 60 and 62, of housing portions 36a and 38a respectively, utilizing adhesive portions 52a and 52b therefor.

FIG. 6 illustrates housing portion 38a having floss material 18b disposed therewithin. Adhesive portion 52b is readily apparent, securing a portion of dental floss 18b, disposed immediately adjacent end 20c thereof, to the interior surface 64 of housing portion 38a.

FIG. 7 illustrates rectangular plastic sheet 66 having waste portions 68 and a useful portion 70. Lines 72 simulate a heat sealed portion defining a closed configuration, confined entirely on surface 74, of plastic sheet 66. Plastic sheet 66 may be fabricated from polyvinylchloride, or other similar material, having a rigid-like property. Dotted lines 32a are shown extending between points 78 and 80 about lines 72. Dental floss portion 18c is shown disposed substantially entirely within lines 82 and pass thereunder so that the floss-like material 18c may be secured to sheet 66, during any heat sealing process.

FIG. 8 illustrates portion 70, shown in FIG. 7, after waste portion 68 has been separated therefrom, as by die cutting or as by tear sealing, well known in the art. Sheet 82 is shown having a corresponding shape to that of portion 70 of sheet 66, shown in FIG. 1. It should be noted that lines 72 describe areas in which sheets 66 and 82 are joined together. End 84, of dental floss 18c, is similarly shown in cross-section, whilst the other end of dental floss 18c is captured in the flange portion 86, and is not protruding therefrom nor may be seen.

FIG. 9 illustrates housing 10b, having tapered ends 14a and 16a. Such housing may be fabricated from a translucent or an opaque rigid plastic material, having the weakened portion shown by dotted lines 32b.

FIG. 10 illustrates housing 10b, having separable portions 36c and 38c. Such separable portions are divided by a weakened portion depicted as dotted lines 32b. Tapered ends 14a and 16a may be fabricated by collapsing the walls of housing 10b, in a thermal forming process. Plastic material 88, comprising an elastomeric compound, fills the entirety of cavity 26d formed within housing 10b.

FIG. 11 illustrates the apparatus shown in FIG. 9, after portions 36c and 38c have been separated at regions adjacent dotted lines 32b, shown in FIG. 10. Material 88, shown extending between points 90 and 92 of housing portions 36c and 38c respectively, has a foreshortened height and width, of the same material, as it shown in FIG. 10.

FIG. 12 illustrates section 36c, shown in FIG. 11, wherein tapered portion 14a entirely seals off housing portion 36c, capturing therewithin elastomeric material 88, at region 94 thereof wherein the elastomeric material adheres to interior wall portions 96. Portion 98 of elastomeric material 88 is shown in its extended form, obtained by stretching, wherein surface 100 is no longer in contact with interior wall portions 102 of housing portion 36c. A similar effect is noted on housing portion 38c, shown in FIG. 11, when housing portions 36c and 38c are disposed apart by the application of manual forces, applied in the direction of arrow 104, upon housing portion 36c, and an opposed force, not shown, upon housing 38c, shown in FIG. 11.

One of the advantages of the present invention is a one-time use dental flossing device which does not require manual manipulation of the dental floss, as by contacting same with the user's hand, prior to its use.

Another advantage of the present invention is a shortened length of dental floss, to which, handles are permanently secured, thereby affording a user with a convenient and simple means for grasping the dental floss and utilizing same.

Still another advantage of the present invention is a dental floss housing which housing maintains the dental floss in a clean, safe and undisturbed condition, following its initial manufacture, which permits the user to easily and quickly make the clean dental floss readily available for use.

Yet another advantage of the present invention is an inexpensive dental flossing device which, in of itself, may be carried about, from place to place, such that the integrity of the cleanliness of the dental floss is not harmed prior to the time in which the user elects to utilize same.

A further advantage of the present invention is a dental flossing device which is simple to manufacture, convenient in its use, rugged in its construction, and which may bear advertising or other descriptive material directly thereupon.

Yet another advantage of the present invention is overcoming the objectional concept of requiring a user to put their hands into their mouths when utilizing dental floss.

Still yet another advantage of the present invention is avoiding the need for a user to wind the dental floss about their fingers, prior to the use thereof.

A still further advantage of the present invention is utilizing shortened lengths of dental floss, as compared to the normal length manually drawn from a spool, thereby eliminating waste.

The present invention utilizes a housing of any desired shape. The housing includes a cavity in which a portion of a floss-like material is disposed. The ends of the floss-like material are secured within the interior walls of the housing and at opposite ends thereof. The housing may be separated into at least two portions as by slidable separation or by breaking the housing along the weakened portion. The length of the floss-like material, stored within the cavity when intact, must be extensible to a length greater than the remaining portions of the floss-like material but remain secured to the interior walls of the separated portions of the housing, after separation. The housing may be fabricated from any rigid or semi-rigid material, such as a plastic material, whilst the floss-like material may be fabricated from a non-stretchable cord-like material or an elastomeric which achieves a final length after extensive forces, disposed in opposite directions, are applied thereto. The portions of the housing obtained after separation may be utilized as handles. The floss-like material, being totally confined within the cavity of the housing, prior to the housing separation operation, maintains the floss-like material in a clean and safe environment. The open ends of the housing, during the manufacturing phase, may be secured together as by heat sealing, or thermal forming, during which steps the free ends of the floss-like material may be captured and secured to the housing portions. Adhesive may be utilized to secure the otherwise free ends of the floss-like material or, in the case of the elastomeric material, the elastomeric material may be adhered—in quasi adhesive fashion—to the interior portions of the housing portions that remain after the elastomeric material is stretched to the desired length and shape required.

Thus, there is disclosed in the above description and in the drawings, an embodiment of the invention which fully and effectively accomplishes the objects thereof. However, it will become apparent to those skilled in the art, how to make variations and modifications to the instant invention. Therefore, this invention is to be limited, not by the specific disclosure herein, but only by the appending claims.

The embodiment of the invention in which an exclusive privilege or property is claimed are defined as follows:

I claim:

1. An oral hygiene device comprising a unitary housing, said housing defining a cavity therewithin, means to separate said housing into at least two portions, a flexible elongatable material, said material being permanently elongated once said material is stretched, said material completely filling said cavity when unelongated, said material having a pair of ends, one of said pair ends being secured within said cavity to one of said at least two portions of said housing, the other of said pair of ends being secured within said cavity to another of said at least two portions of said housing, said material being elongatable so as to have an exposed length equal to the distance separating said two portions when said housing is separated.

2. The apparatus as claimed in claim 1 wherein said means to separate comprises said unitary housing having a weakened portion, said weakened portion being disposed within the periphery of the wall of said housing and encircling same at a location intermediate said pair of ends of said material.

3. The apparatus as claimed in claim 2 wherein said weakened portion comprises a plurality of indentations disposed in spaced apart relationship and extending partially within said wall.

4. The apparatus as claimed in claim 1 wherein said housing comprises a plastic material.

5. The apparatus as claimed in claim 1 wherein said material comprises an elastomeric compound, said compound being extensable.

6. The apparatus as claimed in claim 5 further comprising said elastomeric material filling the entirety of said cavity when said housing defines a single cavity totally encapsulating said elastomeric material.

7. The apparatus as claimed in claim 1 wherein said housing is a right angle cylinder, having a pair of closed ends.

8. The apparatus as claimed in claim 1 wherein said means to separate comprises said housing being frangibly separatable into said at least two portions thereof.

* * * * *